US010499637B2

(12) United States Patent
Mehlhorn et al.

(10) Patent No.: US 10,499,637 B2
(45) Date of Patent: Dec. 10, 2019

(54) **COMPOSITIONS COMPRISING FLAVONOID-CONTAINING EXTRACTS FROM PLANTS OF THE GENUS *CITRUS* AND/OR ISOLATED *CITRUS* FLAVONOIDS AND SPECIFIC CATIONIC SURFACE ACTIVE AGENTS, AND SAID COMPOSITION FOR USE AS AN AGENT FOR TREATING INFESTATIONS WITH HEAD LICE**

(71) Applicant: MEDA AB, Solna (SE)

(72) Inventors: Heinz Mehlhorn, Neuss (DE); Guenter Schmahl, Cologne (DE); Juergen Schmidt, Duesseldorf (DE); Fathy Abdel Ghaffar, Nasr (EG); Khaled Al Rasheid, Riyadh (SA); Saleh Quraishi, Riyadh (SA); Ahmad Al-Farhan, Riyadh (SA)

(73) Assignee: Meda AB (SE)

( * ) Notice: Subject to any disclaimer, the term of this patent is extended or adjusted under 35 U.S.C. 154(b) by 244 days.

(21) Appl. No.: 15/361,090

(22) Filed: Nov. 25, 2016

(65) Prior Publication Data

US 2017/0071202 A1 Mar. 16, 2017

Related U.S. Application Data

(63) Continuation of application No. 13/580,985, filed as application No. PCT/EP2009/064442 on Nov. 2, 2009, now abandoned.

(51) Int. Cl.

| *A01N 43/16* | (2006.01) |
| *A01N 33/12* | (2006.01) |
| *A61K 8/41* | (2006.01) |
| *A61K 8/49* | (2006.01) |
| *A61K 8/97* | (2017.01) |
| *A61K 31/352* | (2006.01) |
| *A61K 31/7048* | (2006.01) |
| *A61Q 17/02* | (2006.01) |
| *A61K 31/353* | (2006.01) |
| *A61K 45/06* | (2006.01) |

(52) U.S. Cl.
CPC ............ *A01N 43/16* (2013.01); *A01N 33/12* (2013.01); *A61K 8/416* (2013.01); *A61K 8/498* (2013.01); *A61K 8/97* (2013.01); *A61K 31/352* (2013.01); *A61K 31/353* (2013.01); *A61K 31/7048* (2013.01); *A61K 45/06* (2013.01); *A61Q 17/02* (2013.01)

(58) Field of Classification Search
None
See application file for complete search history.

(56) References Cited

U.S. PATENT DOCUMENTS

| 5,145,839 A | 9/1992 | Beljanski |
| 6,165,984 A | 12/2000 | Bok et al. |
| 8,097,602 B1 | 1/2012 | Holzer |
| 2005/0019431 A1 | 1/2005 | Modak et al. |
| 2006/0275334 A1 | 12/2006 | Dokic-Gallagher |
| 2008/0193387 A1 | 8/2008 | de Wolff |
| 2009/0011042 A1 | 1/2009 | Willimann et al. |
| 2009/0176890 A1 | 7/2009 | McPartland |
| 2009/0192207 A1 | 7/2009 | Boeckh et al. |
| 2010/0015064 A1 | 1/2010 | Rossel |
| 2010/0068157 A1 | 3/2010 | Ripley |
| 2011/0275582 A1 | 11/2011 | Spring et al. |

FOREIGN PATENT DOCUMENTS

| AU | 2008 101 219 A4 | 2/2009 |
| AU | 2008101219 A4 | 2/2009 |
| CN | 1 013 057 23 A | 11/2008 |
| CN | 101305723 A | 11/2008 |
| CN | 1 01 422 160 A | 5/2009 |
| CN | 101422160 A | 5/2009 |
| DE | 102008004676 A1 | 7/2008 |
| EP | 0352147 A2 | 1/1990 |
| EP | 1032381 A1 | 9/2000 |
| EP | 1 591 123 A1 | 11/2005 |
| EP | 1591123 A1 | 11/2005 |
| EP | 2 081 428 A2 | 7/2009 |
| EP | 2081428 A2 | 7/2009 |
| EP | 2090325 A2 | 8/2009 |
| KR | 2000 002 2375 A | 4/2000 |

(Continued)

OTHER PUBLICATIONS

Abdelatif, H. M., Thesis: "Insecticidal and Antibacterial Activity of Citrus Fruits' Peels and Juices", 2004, 148 pages (Year: 2004).*
Clayton, D. H. et al., The Auk, "Common Grackle Anting with Lime Fruit and Its Effect on Ectoparasites", 1993, vol. 110, No. 4, pp. 951-952 (Year: 1993).*
T. Sasaki et al.: "First Molecular Evidence of Bartonella Quintana in Pediculus humanus capitis (Phthiraptera: Pediculidae), Collected from Nepalese Children", J. Med. Entomo., vol. 43, pp. 110-112 (2006).
E.M.Galati et al: "Biological effects of hesperidin, a citrus flavonoid. (note I): Antiinflammatory and analgesic activity", Il Farmaco, vol. 49, pp. 709-712 (1994).
M.T. Montforte et al.: "Biological effects of hesperidin, a citrus flavonoid. (note II): Hypolipidemic activity on experimental hypercholesterolemia in rat.", Il Farmaco, vol. 50. 595-599 (1995).

(Continued)

*Primary Examiner* — Layla D Berry
*Assistant Examiner* — Bahar Craigo

(57) ABSTRACT

A method for treating an infestation of head lice in a patient in need thereof by killing the head lice and preventing a final development and a hatching of larvae from lice eggs. The method includes applying an effective amount of a composition on the hair of the patient. The composition includes about 0.1 to 1 wt.-% of at least one isolated *Citrus* flavonoid and 2 to 7 wt.-% of at least one cationic surface-active agent. The cationic surface-active agent is selected from a quaternary ammonium salt having one or two linear saturated $C_{8-26}$ alkyl chain(s), wherein the remaining alkyl residues are $C_{1-6}$ alkyl groups, and palmitamidopropyltrimonium chloride.

17 Claims, No Drawings

(56) References Cited

FOREIGN PATENT DOCUMENTS

| KR | 20000022375 A | 4/2000 |
|---|---|---|
| NZ | 545068 A | 12/2008 |
| WO | 199848625 A1 | 11/1998 |
| WO | WO 98/48625 A1 | 11/1998 |
| WO | 2005009352 A2 | 2/2005 |
| WO | 2006116778 A2 | 11/2006 |
| WO | WO 2006/116778 A2 | 11/2006 |
| WO | 2008009956 A1 | 1/2008 |
| WO | 2008038108 A2 | 4/2008 |
| WO | WO 2008/038108 A2 | 4/2008 |
| WO | 2008056365 A2 | 5/2008 |
| WO | WO 2008/056 365 A2 | 5/2008 |
| WO | 2008101131 A1 | 8/2008 |
| WO | 2009105617 A1 | 8/2009 |

OTHER PUBLICATIONS

S.Rajkumar et al.: "Bioactivity of flavonoid compunds from *Poncirus trifoliata* L. (Family: Rutaceae) against the dengue vector, *Aedes aegypti* L. )(Diptera: Culicidae)", Parasitol. Res. vol. 104, pp. 19-25 (2008).
A. Ortuno et al,: "Citrus paradisi and Citrus sinensis flavonoids: Their influence in the defence mechanism against Penicillium digitatum", Fod chemistry, vol. 98, pp. 351-358 (2006).
D. Robinson et al.: "Potential role of head lice *Pediculus humanus capitis*, as vectors of *Rickettsia prowazekii*", Parasitol Res, No. 90, pp. 209-211 (2003).
T. Sasaki et al: "First Molecular Evidence of *Bartonella quintana* in *Pediculus humanus capitis* (Phthiraptera: Pediculidae), Collected from Nepalese Children", J. Med. Entomol., vol. 43, pp. 110-112 (2006).
E. M. Galati et al: "Biological effects of hesperidin, a citrus flavonoid. (note 1): Antiinflammatory and analgesic activity", Il Farmaco, vol. 49, pp. 709-712 (1994).
M. T. Monforte et al.: "Biological effects of hesperidin, a citrus flavonoid. (note II): Hypolipidemic activity on experimental hypercholesterolemia in rat.", Il Farmaco, vol. 50, pp. 595-599 (1995).
S. Rajkumar et al: "Bioactivity of flavonoid compounds from *Poncirus trifoliata* L. (Family: Rutaceae) against the dengue vector, *Aedes aegypti* L. (Diptera: Culicidae)", Parasitol. Res. vol. 104, pp. 19-25 (2008).
F. A. Macias et al: "Natural biocides from citrus waste as new wood preservatives", www.regional.org.au (2005).
A. Ortuno et al: "*Citrus paradisi* and *Citrus sinensis* flavonoids: Their influence in the defence mechanism against *Penicillium digitatum*", Food Chemistry, vol. 98, pp. 351-358 (2006).
R. C. Pepe et al.: "International Cosmetic Ingredient Dictionary and Handbook", The Cosmetic, Toiletry, and Fragrance Association, Washington, pp. 2013 and 2544 (1997).
Swindon Pulse Wholefoods Co-Operative: "Citricidal Grapefruit Seed Extract—the A-Z for "All-in-One" protection", www.swindon-pulse.co.uk, pp. 1-3 (2005).
Th. Von Woedtke et al.: "Aspects of the antimicrobial efficacy of grapefruit seed extract and its relation to preservative substances contained", Pharmazie, vol. 54, No. 6, pp. 452-456 (1999).
G. R. Takeoka et al.: "Identification of Benzalkonium Chloride in Commercial Grapefruit Seed Extracts", Journal of Agricultural and Food Chemistry, vol. 53, No. 19, pp. 7630-7636 (2005).
"DM Drogerie Markt, Czech Republic Brand DM Balea Haircare Lotusblüte & Orange Volume Spray Treatment", The Global New Products Database, MINTEL, London (UK), p. 1 (2009).
Anonymous: "Citricidal Grapefruit Seed Extract", Nutriteam, p. 1 (2015).

\* cited by examiner

COMPOSITIONS COMPRISING FLAVONOID-CONTAINING EXTRACTS FROM PLANTS OF THE GENUS *CITRUS* AND/OR ISOLATED *CITRUS* FLAVONOIDS AND SPECIFIC CATIONIC SURFACE ACTIVE AGENTS, AND SAID COMPOSITION FOR USE AS AN AGENT FOR TREATING INFESTATIONS WITH HEAD LICE

CROSS REFERENCE TO PRIOR APPLICATIONS

This application is a continuation of application Ser. No. 13/580,985, filed on Jan. 24, 2013, which is a U.S. National Phase application under 35 U.S.C. § 371 of International Application No. PCT/EP2009/064442, filed on Nov. 2, 2009. The International Application was published in English on May 5, 2011 as WO 2011/050857 A2 under PCT Article 21(2).

FIELD

The invention relates to a composition having anti-lice properties comprising effective amounts of one or more specific quaternary ammonium salt surface active agent(s) (named monoalkyl, dialkyl quat and amidoquat, respectively, in the context of the present invention) in combination with flavonoid-containing extracts obtained from plants of the species *Citrus* and/or isolated *Citrus* flavonoids. Further, the invention relates to said composition for use in a method for treating infestation with head lice, and said composition for use as a medicinal product or cosmetic product.

BACKGROUND

Head lice (*Pediculus humanus capitis*) are parasitic insects that live permanently on humans. Lice occur worldwide and are remarkably widespread in children aged between 3 and 15 years. In many industrialized countries the cases of infested individuals have been observed to increase significantly during the last years. Lice infestations have remained a troublesome problem.

Lice suck blood every few hours. This irritates the skin and infested persons suffer from itching sensations. Children with lice may become sleepless and nervous. Scratching the skin may lead to secondary bacterial infections. The closely related body louse (*Pediculus humanus corporis*) has the potential to spread serious agents of diseases. Experimental infections and epidemiological studies have revealed that also head lice may act as vectors of bacteria (Robinson D., Leo N., Provic P., Barker S. (2003) Potential role of *Pediculus humanus capitis* as vectors of *Rickettsia prowazeki*. Parasitol Res 90:209-211; Sasaki T., Pondel S., Isawa H., Hayashi T., Sekia N., Tomita T., Sawabe K., Kobayashi M., First molecular evidence of *Bartonella quintana* in *Pediculus humanus* capitis, collected from Nepalese children. J. Med. Entomol. 43:110-112, (2006)). Parents in concern about their children often undertake enormous efforts to eradicate the parasites.

Traditionally lice have been treated with insecticidal pesticides. Most of the lice-killing chemicals are toxicants acting on the nervous system of insects, e.g. by inhibiting acetylcholinesterases. Insecticides in lice medications are organochlorines, e.g. lindane and DDT, natural pyrethrum or synthetic pyrethroids, e.g. permethrin or resmethrin, often in combination with the monooxygenase inhibitor piperonyl butoxide, the carbamate ester carbaryl, and the thiophosphate ester malathion, and fipronil. Recent patent applications describe topical avermectin (EP2091325A2), 1-N-arylpyrazole and amitraz (US 2009/192207 A1), clothianidin (CN 1011422160 A), spinosad (CN 101305723 A) and also an oral application of ivermectin.

Insecticidal lice products, however, are generally and increasingly thought of with caution, especially when young children are treated with such toxins. Most parents fear to apply to their children harmful insecticidal chemicals. Poisoning does not require ingestion of the product, since anti-lice chemicals readily may be absorbed through the skin.

Nowadays, lice products being free of any insecticides are clearly preferred by parents and many physicians and pharmacists. Medications with lice killing effects based on neurotoxic, immunological, metabolic or other pharmaceutical effects, and this includes the insecticides, are classified as pharmaceutical drugs by EU authorities. The majority of these medications require prescription. By contrast, medicinal products that constitute a growing market, are available over the counter. Medicinal products, however, must only have a physical/mechanical effect on the lice, e.g. kill lice by suffocation.

Home remedies to suffocate lice with various plant oils have been reported to function unreliably, as lice immersed in oils and thereby deprived from oxygen are able to survive up to several hours. Medications containing coconut oil and coconut fatty acid derivates also have been found not to be sufficiently effective.

A suffocation mode of activity has been ascribed to licicidal medications based on silicone/siloxane oils (patents WO 2009/105617, EP 2081428 A, NZ 545068). Cyclomethicone, dimethicone, and other types of silicones and most of them in combination with a plant oil derivative are marketed as non-prescription medicinal products. However, silicone-containing formulations distributed in the hair turned out to be highly flammable. Incidences have occurred, were the entire skin of the head burned away. It is not acceptable to treat a child with a silicone product, which possibly could ruin the live, solely for reason to eliminate a few insects. Silicone medications also have the disadvantages to be very sticky to the hair, and to require, after treatment, several washings with normal shampoo to remove the medication. Some silicone preparations bear even more hazardous risks. DE 102008004676 by Oystershell teaches a formulation of a siloxane in combination with more than 50 weight-percent of saturated linear or branched C10 to C22-carbon chains. If only tiny amounts of this formulation would be inhaled during treatment of the head, it can be deduced from available information on these molecules that the child would suffer serious damages of the lung and possibly even could die.

Herbal preparations are assumed by most people to be in general less harmful than synthetic chemicals, though in some cases this is questionable from a scientific view. Pharmaceutical producers offer lice treatments containing various active ingredients from plants. Many herbal products are based on essential oils, and the modest capacity of essential oils and certain terpenes of the oils to kill insects is known from numerous studies. Several patent applications claim the use of essential oils and terpenes as lice treatments, e.g. limonene (KR 20000022375 and US 2009/176890) or a mixture of essential oils (WO 2008/101131). Also combinations of neem oil and essential oils, e.g. those from anise, tea tree and other *Eucalyptus* oils and lavender oils have been proposed to treat lice (AU 2008101219). Essential oils, however have the serious disadvantage to be skin irritating and sensitizing. Due to that, the EU legislation 2003/15/EC Directive requires that products containing certain allegedly allergenic essential oil terpenes have to be labelled with a warning note that the product may cause allergies. Several essential oil constituents are skin penetrating neurotoxins, notably anethol from anise or star anise, and commercialized products containing these substances are critical for the health of children. Moreover, due to the pharmaceutical activity of terpenes, these anti-lice products strictly are to be classified as pharmaceutical drugs, not as medicinal products.

For other herbal medications, e.g. based on cassia or carrot seed oil (WO 2008/056365; US 2009/176890, AU 2008101219), none or sparse evidence of their efficacy against lice infestation has been documented in scientific studies.

With nearly all marketed licicidal products the parents are encouraged to use in addition special fine-toothed louse combs to remove remaining and still surviving lice. Hence, producers themselves presume that their medications are not 100% effective. In fact, patients often report that viable lice and/or eggs have survived chemical treatments. Thus, after application of a medicinal treatment, the hair also has to be combed to securely get rid of all lice, which is a very cumbersome and time-consuming procedure not well-tolerated by children.

In consequence, the art continues to seek improvements in better product formulations to combat lice.

Doubtless, there is a strong need for a head lice medication that is highly effective against the parasites, that is safe and easily to use.

SUMMARY

An aspect of the present invention is to provide a treatment for infestation with lice having no toxicity, that exerts a lice killing mechanism based on a physical mode of action, and that is not prone to development of resistance. An additional aspect of the present invention is that the residuals of the medication must be environmentally safe, and is expected to enable a user-friendly application consisting in a short treatment time not exceeding much that for an ordinary shampoo used for normal hair cleaning by non-infested persons.

In an embodiment, the present invention provides a method for treating an infestation of head lice in a patient in need thereof by killing the head lice and preventing a final development and a hatching of larvae from lice eggs. The method includes applying an effective amount of a composition on the hair of the patient. The composition includes about 0.1 to 1 wt.-% of at least one isolated *Citrus* flavonoid and 2 to 7 wt.-% of at least one cationic surface-active agent. The cationic surface-active agent is selected from a quaternary ammonium salt having one or two linear saturated C8-26 alkyl chain(s), wherein the remaining alkyl residues are C1-6 alkyl groups, and palmitamidopropyltrimonium chloride.

DETAILED DESCRIPTION

The invention provides a composition comprising a flavonoid-containing extract from plants of the species *Citrus* and/or one or more isolated *Citrus* flavonoids in combination with at least one cationic surface-active agent selected from the group consisting of quaternary ammonium salts having one or two $C_{8-26}$ alkyl chain(s) (in the following named monoalkyl or dialkyl quats) and quaternary ammonium salts having one $C_{8-26}$ fatty acid being bound to the ammonium nitrogen via an amide bond (in the following named amido quats).

One of the constituents of the composition according to the present invention are flavonoids. Flavonoids are natural polyphenols with a 2-phenylbenzopyrone (2-phenyl-benzochromen-4-one) structure. They are often called bioflavonoids, indicating that they are plant derived, e.g. obtained from citrus fruits (genus Rutaceae, species *Citrus*), and because of their beneficial health effects. Naringin (7-[[2-O-(6-desoxy-α-L-mannopyra-nosyl)-β-D-glucopyranosyl]oxy]-2,3-dihydro-5-hydroxy-2-(4-hydroxy-phenyl)-4H-1-benzopyran-4-one), hesperidin ((2S)-7-((6-O-(6-desoxy-α-L-mannopyranosyl)-β-D-glucopyranosyl)oxy)-2,3-dihydro-5-hydroxy-2-(3-hydroxy-4-methoxyphenyl)-4H-1-benzopyran-4-one) and their aglycons naringenin ((S)-2,3-dihydro-5,7-dihydroxy-2-(4-hydroxyphenyl)-4H-1-benzopyran-4-one) and hesperetin ((S)-2,3-dihydro-5,7-dihydroxy-2-(3-hydroxy-4-methoxyphenyl)-4H-1-benzopyran-4-one) are constituents of grapefruits and other *citrus* fruits, and have very low toxicity. Due to their bitter taste, they are used as an additive for certain beverages. Polyphenols protect the body against cell-destroying effects of free radicals and *citrus* fruit consumption is associated with a reduction in cancer incidence. Flavonoids also protect vascular cells, exhibit cholesterol-lowering effects and act anti-inflammatory (Galati E. M. et al. 1994, Biological effects of hesperidin, a *citrus* flavonoid (note I): anti-inflammatory and analgesis activity. In: Farmaco vol. 40, p 709-712; Montforte M. T. et al. 1995: Biological effects of hesperidin, a *citrus* flavonoid (note II): hypolipidemic activity on experimental hypercholesterinemia in rat. In: Farmaco vol. 50, p 595-599).

Naringin is a peculiar flavonoid, which can be extracted from grapefruit seed and pulp. Naringin displays several health-related properties of flavonoids. Grapefruit flavonoids are under study as therapies against inflammation, tumor (EP 0352147) and liver diseases (EP 1032381), treatment of cough (EP 1591123) and in alternative medicine are applied to treat against a broad range of diverse diseases.

A putative insecticidal activity of naringin is of interest in the present context. A fraction containing naringin in acetonitrile has been collected from high pressure liquid chromatography and this fraction has been reported to kill mosquito larvae (Rajkumar S., Jebasan A., Bioactivity of flavonoid compounds from *Poncirus trifoliata* L. (Family: Rutaceae) against the dengue vector, *Aedes aegypti* L. (Diptera: Culicidae). Parasitol. Res. 104:19-25, (2008)). However, the results were not corroborated by experiments in our laboratory where even a thousand fold higher concentration of naringin, but without acetonitrile in the assay, did not kill *Aedes aegypti* larvae. Naringin itself does not have an insect killing activity. Volatile essential oils, e.g. limonoids, and non-volatile flavonoids of extracts obtained from *citrus* fruit have been suggested to protect the fruits against fungi and insects (Macias F. A. at al., Natural biocides from *Citrus* waste as new wood preservatives, www.regional.org.au (2005)). Polymethoxyflavones are more active than the flavones against fungi (Ortuno A. et al. *Citrus paradisi* and *Citrus sinensis* flavonoids: Their influence in the defence mechanism against *Penicillium digitatum*. Science Direct-Food Chemistry 98:351-358, (2005)).

The second constituent of the composition according to the present invention are specific cationic surface-active agents. Compounds with cationic moieties typically are used for conditioning in hair care, though silicone compounds gained a dominant role for this purpose. Hair bears negative charges to which cationic agents can be bound in order to impart an antistatic effect and to obtain a smooth hair surface. Cationic emulsifiers comprise one or two charged nitrogen atoms and one or two alkyl chains. To the present state of the art, monoalkyl and dialkyl quats and amidoquats are not known to have any licidical effect have not been employed for treating lice infestations.

Surprisingly it was found by the inventors that flavonoid-containing extracts obtained from plants of the species *Citrus* and/or one or more of isolated *Citrus* flavonoids in combination with monoalkyl or dialkyl quats and/or amidoquats exert a strong licicidal effect. Thus, the present invention was accomplished.

The composition of the present invention readily infiltrates the tracheae and tiny tracheolae and thereby irreversibly blocks the uptake of oxygen by the louse. The inventive composition also dissolves barrier substances plugging the breathing pores of the eggs. This leads to drying out of the developing embryo. These licicidal effects are not observed when the monoalkyl- or dialkyl quats and/or amidoquats or flavonoid-containing *Citrus* extracts and/or isolated *Citrus* flavonoids are used as single compounds.

A further advantage of the present invention is that the active principle does not contain noxious constituents, which might harm the health of treated humans.

Flavonoids which are contained as main components in the *Citrus* plant extracts used according to the invention are naringin, naringenin, hesperetin and hesperidin. These flavonoids are typically contained in extracts obtained form plants of the genus *Citrus*, such as grapefruit, pomelo, orange, bitter orange, blood orange, bergamot orange, lemon, key lime, lime, clementine, satsuma, tangelo, tangerine, mandarin orange and kumquat. Most preferably extracts obtained from grapefruit, orange and lemon are used according to the invention. Such extracts can be obtained from *Citrus* fruits or fruit parts such as pulp, peels or kernels by procedures known to the one skilled in the art. Typically, the plant parts are extracted with a suitable solvent such as e.g. petrol ether, cyclohexane, hexane or pentane, in order to remove unwanted essential oils. The solvent fraction is then discarded and the plant material is dried and then extracted with a suitable solvent such as methanol or ethanol. Subsequently the extract is concentrated until a syrup is obtained, and then the flavonoids are precipitated by adding a suitable acid, e.g. acetic acid. The precipitate is then washed with e.g. diluted acid such as diluted acetic acid, if desired, and dried. Flavonoid-containing extracts of *Citrus* plants are also commercially available, e.g. from Furfural Espanol S.A. They may be used according to the invention as a dry extract or as a suspension or solution in a suitable solvent such as glycerol. Grapefruit dry extract typically contains up to 50% by weight of naringin based on the total content of flavonoids.

According to the invention the *Citrus* flavonoids naringin, naringenin, hesperetin and hesperidin may also be used as isolated compounds for preparing the composition, either a single compounds or as a mixture of one or more compounds. They may also be used in admixture with the flavonoid-containing *Citrus* extract defined before. Naringin and hesperidin are the most preferred flavonoids according to the invention. These *Citrus* flavonoids are commercially available e.g. from Furfural Espagne S.A. or can be manufactured by known processes.

Preferred compositions include at least 0.05% by weight flavonoid or mixtures of flavonoids, preferably at least 0.1%, and most preferably at least about 0.2% by weight based on the total composition. Typically the maximum total amount of the flavonoids in a composition according to the invention is 0.5-10%, preferably 0.5-15%, most preferably about 0.5-1% by weight. These amounts refer to the isolated flavonoids. If *Citrus* extract is used for preparing the composition, the amount of extract to be added to the composition is calculated based on the amount of flavonoids contained in the extract in order to achieve the flavonoid contents defined above.

Preferred compositions according to the invention include at least about 0.1% by weight of the cationic surface active agent as defined in the claims, preferably at least about 0.5% by weight, and most preferably at least about 1% by weight of the cationic surface active agent based on the total composition. Typically the amount of cationic surface active agent is about 2-25%, more preferably about 2-10%, most preferably about 2-7% by weight.

The surface active agents are selected from quaternary ammonium salts having one or two linear saturated C8-26 alkyl chain(s) (named monoalkyl and dialkyl quats, respectively) and quaternary ammonium salts having one C8-26 fatty acid being bound to the ammonium nitrogen via an amide bond (amido quats). In dialkyl quats, the two long alkyl chains may be the same or different. Preferred long alkyl chains of the mono- and alkyl quats are fatty alcohol residues, in particular stearyl, cetyl and behenyl.

The remaining alkyl residues of the quaternary ammonium salt are short-chain alkyl groups, in particular C1-6 alkyl groups, which may be linear or branched, e.g. methyl, ethyl or n-propyl, i-propyl, n-butyl, i-butyl, sec.-butyl, tert.-butyl groups, pentyl groups or hexyl groups. They may be the same or different. Preferably these remaining alkyl groups are methyl or ethyl, most preferably methyl.

The fatty acids for forming the amide bond of the amidoquat are typically $C_{8-24}$ fatty acids, which are linear and which may have one or more double bonds in the carbon chain. Examples for the fatty acid the residue is derived form are caprylic acid, caproic acid, pelargonic acid, decanoic acid, undecanoic acid, lauric acid, stearic acid, palmitic acid, oleic acid, linolienic acid, linoleic acid, arachidonic acid, elaidinic acid, myristic acid, margaric acid, arachidic acid, behenic acid, pentadecanoic acid.

The counter-anions of the ammonium salts are selected from bases of strong or weak inorganic or organic acids such as halogenides (chloride, bromide, iodide, fluoride, preferably chloride), sulphate, nitrate, phosphate, acetate, toluenesulfonate, sulfonate, trifluoracetate, carbonate, bicarbonate, dihydrogenphosphate, hydrogendiphosphate, benzoate and other usually employed anions. Most preferred are halogenides and in particular chlorides.

Preferred monoalkyl quats are behentrimonium chloride (Docosyl-trimethyl-ammonium chloride) and cetrimonium chloride (hexadecyl-trimethyl-ammonium chloride). Preferred dialkyl quats are dicetyldimonium chloride (dihexadecyl-dimethyl-ammonium chloride) and distearyl-dimonium chloride (dimethyl-dioctadecyl-ammonium chloride). Preferred quats used in the inventive composition are amidoquats. A preferred amidoquat and at the same time the most preferred of all cationic surface active agents used according to the invention is palmitamidopropyl-trimonium chloride.

The cationic alkyl quats are commercially available preparations, e.g. Varisoft PATC (manufactured by EVONIK), Incroquat™ HO or OCS (manufactured by Croda). These products may contain other ingredients, which may also be present in the composition according to the present invention if the commercially available quats and/or amidoquats are used.

The composition of the present invention preferably is adapted for application as a shampoo. The present invention, however, also comprises formulations, non-exhaustively, as mousse, gel, lotion, liquid, spray, aerosol, hair spray, paste, powder, hair conditioner or other compositional forms. The invention also comprises formulations such household agents selected form the group consisting of washing solution, spray or powder for treatment of textiles, beddings, carpets or furniture. Immersion solutions for lice combs, that may be used successively for several individuals, and washing additives for lice eliminating treatments of clothing or bedding textiles are also comprised in the present invention.

The shampoo formulation would typically be left in the hair for about 5 minutes to 1 hour. Then the product and dead lice are rinsed out from the hair with warm water. The application of the inventive formulation may be repeated after 8 to 10 days, if necessary, though typically a single treatment will be sufficient to eradicate the lice infestation.

An additional advantage of the quat(s) used in the composition of the present invention is the known hair conditioning effect of this substance. When the treatment against living lice is finished, the user wishes to remove all nits, i.e. shells of the lice eggs glued to the hair. To achieve this the hair typically is intensely combed. The act of combing generates negative charges so that the similarly charged hair fibers repulse each other. Alkyl quats or amidoquats neutralize the negative charges, reduce the flyaway of the hair and thereby allow to easily comb the smooth lying hair. Also, it is an important advantage of the quats used in the composition of the present invention that the smoothening the hair surface makes it significantly easier to strip away the nits from the hair fibers.

The composition according to the invention may be used as a cosmetic product, medicinal product or pharmaceutical product. It is used for treating infestation with head lice, and may be used by adults, youths and children.

The invention also comprises a composition as defined before for use in a cosmetic or medical treatment of infestation with head lice. In different countries compositions intended for treating infestation with head lice are classified according to local law as medical, cosmetic or medicinal product, and all these uses are comprised in the present invention.

Production of a Medication According to the Invention

The production of the claimed anti lice medication may be started with the dissolution of a *Citrus* extract or powder containing naringin, naringenin, hesperidin and/or hesperetin or of one or more of these isolated flavonoids with the quat fluid. The mixture forms a complex of both substances, and a colour development from faint brownish of the flavonoid powder to an intense yellow-brown coloration of the solution can be observed. The colour intensity of this insecticidal complex can be measured by spectrophotometry, e.g. for purpose of in-process quality control.

To obtain a shampoo formulation the insecticidal complex is mixed with different additives. Shampooing of the head ensures uniform distribution of the medication all over the hair.

The composition according to the invention may be any suitable chemical entity that is compatible with the hair and the skin physiology (Pepe R. C., Wenniger J. A., McEwen G. N. (eds.) 2000, International Cosmetic Ingredient Dictionary and Handbook. Cosmetics, Toiletry and Fragrance Association, Washington).

The composition of the invention may also comprise other insect-killing substances which are known in the art, such as those mentioned in the introductory part of this description.

The composition of the present invention may further comprise usual suitable additives and ingredients which are generally used in medicinal products or cleaning compositions.

Examples are non-ionic, anionic amphoteric, zwitterionic or cationic surfactants other than the quats defined above, which can serve to boost or stabilize the foaming of a shampoo, to emulsify other constituents of the formulation, or compounds added for purpose of hair and skin cleansing. Examples include, but are not limited to, sodium laureth sulfate, ammonium laureth sulfate, cocamidopropyl betain and other N-alkyl betaines, sulphobetaines, lauryl sulfates, ester linked sulphonates, alkyl carboxylates, N-acyl sarcosinates, N-substituted alkyl amides, soaps made from fatty acids with alkali, polyglyceryl-3-caprate, lauryl glucoside, glyceryl laurate.

Examples of emulsifiers and emollients which may be added are, but are not limited to, cocoamido ethyl betaine, cetyl betaine, lauramidopropyl betaine, disodium cetearyl sulfosuccinate, disodium oleoampho-dipropionate, lauramide DEA, cetyl phosphate, potassium cetyl phosphate, glycerol monooleate, glyceryl stearate, cetearyl glucoside, sorbitan monopalmitate, sorbitan trioleate, sorbitan sesquioleate, glyceryl trioleate, triglyceryl diisostearate, sucrose distearate, sucrose cocoate, polyoxyethylene monostearate, sucrose distearate, polyethylene glycol monostearate, capric/caprylic triglyceride, cetyl palmitate, cetyl alcohol, isopropyl stearate, glyceryl mono or dilaurate, isopropyl myristate, stearoyl-2-lactylate and polyoxyethylene oleyl ether.

Vehicles which may be used according to the invention include, but are not limited to, water, ethanol, glycerol, isopropanol, propylene glycol, butylene glycol and silicones. Preferably, the vehicle is water.

A product according to the present invention may also comprise other hair conditioning agents that alter the wet and dry combing properties, the appearance, feel or styling of the hair.

Examples include, but are not limited to, chitosan and polyquaterniums, cationic amino acids, cyclomethicone, dimethicone, amodimethicone, biotin, panthotenate, dicaprylyl ether and hydrolyzed proteins. Additives to improve the hair texture may be, but are not limited to, glycerol, polyethylene glycol, propylene glycol, glucose, sucrose and sorbitol.

Preferably the pH of a composition of this invention is in the range from 4.0 to 8.5, and most preferably between 4.5 and 6.0. To adjust the desired pH, usual organic or inorganic acids or bases or buffers may be added. Examples for these pH adjusting agents are acetic acid, formic acid, citric acid, lactic acid, oxalic acid, glutaric acid, adipic acid, fumaric acid, boric acid, phosphoric acid and salts thereof, potassium or sodium hydroxide, or ammonia may be added.

Antioxidants may be included in the formulation in order to prevent the degradation caused by oxidation. Antioxidants include, but are not limited to ascorbic acid, tocopherol, acetyl cysteine, cysteine, gallates, natural polyphenolic compounds and butyl hydroxytoluene.

A formulation of the present invention may be stabilized with preservatives to inhibit microbial growth. Examples include, but are not limited to, ethanol, benzoic acid, benzyl alcohol, chlorohexidine, germaben, parabens, sorbic acid, and phenoxyethanol.

Examples of further adjuvants include, but are not limited, to chelating agents, polymers to stabilize and prevent physical separation of the formulation, thickeners, fragrances and dyes.

EXAMPLES

The invention will be described further by consideration of the following examples. There exist many possibilities of formulations, thus the examples provided are only a few of the possible combinations. The quantities referred herein are measured by weight of the total composition.

Production of Grapefruit Extract

Dried seeds or peels of grapefruits (10 kg) are extracted with 60 kg petrol ether at 50° C. for 4 hours in order to remove unwanted essentials oils. The petrol ether fraction is discarded and the plant material is dried and then extracted with methanol for at least 2 hours. The methanolic extract is concentrated by evaporation until a sirup consistency is obtained. Acetic acid (6%) is added to precipitate the flavonoids. The precipitate is washed with 6% acetic acid and dried.

Examples of Formulation

In order to obtain a medicinal shampoo-product the compounds were added one after the other and then heated to 70° C.:

1. Licicidal Medication as Shampoo:
   1.0% naringin, 3.0% palmitamidopropyltrimonium chloride, 12.0% sodium laureth sulfate, 8.0% polyglyceryl-3-caprate, 2.0% glycerol, 2.0% dicaprylyl ether, 0.3% benzyl alcohol, 0.2% benzoic acid, 0.25% sorbic acid and water purificata ad 100%.
2. Licicidal Medication as Shampoo:
   0.5% naringin, 0.5% hesperidin, 4.0% behentrimonium-chloride, 12% cocoamidopropyl betain, 8.0% lauryl glucoside, 7.0% glycerol, 1.0% dicaprylyl ether, 0.3% benzyl alcohol, 0.2% benzoic acid, 0.12% sorbic acid and water purificata ad 100%.
3. Licicidal Medication as Shampoo:
   0.4% naringin, 3.0% palmitamidopropyltrimonium chloride, 10.0% lauryl glucoside, 9.0% polyglycerol-3 caprate, 7.0% cocoamidopropyl betain, 5.0% glycerol, 2.0% glyceryl laurate, 1.0% dicaprylyl ether, 0.6% benzoic acid, 0.12% sorbic acid and water purificata ad 100%.
4. Licicidal Medication as Hair Spray
   0.5% hesperidin, 3.0% distearyldimonium chloride, 19% alcohol denat. And water purifcata ad 100%.
5. Licicidal Spray Product to Treat Textiles Against Lice
   0.5% hesperidin, 3.0% dicetyldimonium chloride, 19% alcohol denat. And water purifcata ad 100%.

Examples of In-Vitro Assays with Head Lice

Head lice, *Pediculus humanus capitis*, were obtained by combing infested children from whom assent and consent from the parents had been obtained.

Lice were used for the experiments mostly immediately, but not later than 4 hours after removing from the head. Adult lice, mixed sexes, were fully immersed in the test solutions for 3 to 15 minutes, then thoroughly rinsed with plenty of water to remove any residuals of the test medication. Three replicates of 5 or 10 lice each, plus one control for each batch of lice, were used for any test formulation. The lice were transferred to dry filter paper and kept for observation for up to 24 hours.

Test 1

The solutions were formulated by addition of the tests substances listed in Table 1 to a basic solution consisting of 10% lauryl glucoside, 5% glycerin and purified water ad 100% and adjusted to pH 6.0 with citric acid. In each test solution 5 lice were incubated, in the controls consisting of the basic solution without any additions 10 lice were incubated. The vitality of the lice is recorded as "mobile" when the louse crawled over the filter paper, as "immobile" when the louse did not crawl, but eventually showed slow movements of one or more legs, and/or peristalsis of the intestine.

"Dead" means that neither movements of the legs nor of the intestine were observed.

At 30 min only mobile or immobile lice were observed, whereas dead lice were observed only at 120 and 360 min.

|  | Vitality of the lice after | | |
| --- | --- | --- | --- |
|  | 30 min mobile/ immobile | 120 min mobile/ dead | 360 min Mobile/ dead |
| 1.0% naringin | 5/0 | 5/0 | 5/0 |
| 1.0% naringenin | 5/0 | 5/0 | 5/0 |
| 0.5% naringin + 0.5% naringenin | 5/0 | 5/0 | 5/0 |
| 1.0% hesperetin | 5/0 | 5/0 | 5/0 |
| 1.0% hesperidin | 5/0 | 5/0 | 5/0 |
| 2.0% palmitamidopr. | 5/0 | 5/0 | 4/1 |
| 2.0% behentrim. | 5/0 | 5/0 | 5/0 |
| 1.0% naringin + 2.0% palmitamidopr.* | 0/5 | 0/5 | 0/5 |
| 1.0% naringenin + 2.0% palmitamidopr. | 0/5 | 0/5 | 0/5 |
| 1.0% hesperidin + 2.0% behentrim.** | 0/5 | 1/4 | 1/4 |
| Control with basic solution (10 lice) | 10/0 | 10/0 | 10/0 |

*palmitamidopr. means palmitamidopropyltrimonium chloride
**behentrim. means behentrimonium chloride Test 1 demonstrates that flavonoids and alkyl quats alone did not kill the lice. The combination of a flavonoid and an alkyl quat efficiently killed the lice.

Test 2

The inventive composition was formulated as a shampoo as given in formulation example 3. For control, lice were incubated in the shampoo basic formulation of example 3, but without additions of a flavonoid or a quat. 12 lice were incubated in each test formulation. The vitality of the lice is recorded as "mobile" when the louse crawled over the filter paper, as "immobile" when the louse did not crawl, but eventually showed slow movements of one or more legs, and peristalsis of the intestine. "Dead" means that neither movements of the legs nor of the intestine were observed.

|  | Vitality of the lice after | | |
| --- | --- | --- | --- |
|  | 30 min mobile/ immobile | 120 min mobile/ dead | 360 min mobile/ dead |
| shampoo with Naringin + palmitamidopr. | 0/12 | 0/12 | 0/12 |
| shampoo without additions for control | 9/3 | 10/2 | 12/0 |

In Vitro Test with Eggs (Nits) from Head Lice

Hair with eggs (nits) was cut off from untreated heads, and, by inspection by microscopy, eggs still having a closed operculum were selected for the assays. Hair material with attached 70 eggs was incubated by immersion a) in shampoo formulation example 3 or
b) in water for control for 15 min, then rinsed with water and stored for 10 days in an incubator at 32° C. and a relative humidity of 70%.

Results: Inspection at day 10 for hatched larvae revealed that 34% of control eggs had developed larvae which were found to be hatched from the eggs in the control, whereas no larvae had hatched in the treatment group. The shampoo based on the inventive formulation completely prevented a final development and hatching of larvae from the eggs.

In Vivo Tests with Lice Infested Individuals

A study has been carried out at the Department of Parasitology of the Cairo University with head lice infested individuals using a shampoo of the present invention. In an Egyptian village 16 girls and 4 boys harbouring a natural lice infestation were treated with consent of the parents and children with formulation example 3. The shampoo was distributed in the hair and left for 10 minutes in 10 children and for 20 minutes in the other 10 children. After treatment the shampoo was rinsed from the hair and the effluent was poured through a fine mesh to collect lice. Then the hair were intensely combed with a nit-comb, to collect any remaining lice.

Results: all lice obtained from the persons treated by application of a shampoo of the inventive formulation were dead.

The present invention is not limited to embodiments described herein; reference should be had to the appended claims.

What is claimed is:

1. A method for treating an infestation of head lice in a patient in need thereof by killing the head lice and preventing a final development and a hatching of larvae from lice eggs, the method comprising:
    applying an effective amount of a composition on the hair of the patient, the composition comprising:
        about 0.1 to 1 wt.-% of at least one isolated *Citrus* flavonoid selected from the group consisting of naringin, naringenin, hesperetin, and hesperidin; and
        2 to 7 wt.-% of at least one cationic surface-active agent selected from the group consisting of palmitamidopropyltrimonium chloride and behentrimonium chloride.

2. The method as recited in claim 1, wherein the at least one cationic surface active agent is palmitamidopropyltrimonium chloride.

3. The method as recited in claim 1, wherein the composition is formulated as a shampoo, a spray, an aerosol, a lotion, a hair conditioner, a gel, a mousse, or as a powder.

4. The method of claim 1, wherein the composition further comprises 92 to 97.9 wt.-% of additives consisting of:
    at least one surfactant selected from an ionic surfactant, an anionic amphoteric surfactant, a zwitterionic surfactant, and a cationic surfactant, which are each respectively not the at least one cationic surface-active agent,
    at least one of an emulsifier and an emollient,
    at least one vehicle,
    at least one hair conditioning agent,
    at least one preservative, and
    optionally, at least one of an insect killing substance, an antioxidant, a pH adjusting agent, and an adjuvant,
    wherein, the respective wt.-%'s add to 100 wt.-%.

5. The method of claim 1, wherein the at least one isolated *Citrus* flavonoid comprises naringin and the at least one cationic surface active agent comprises palmitamidopropyltrimonium chloride.

6. The method of claim 1, wherein the at least one isolated *Citrus* flavonoid comprises naringenin and the at least one cationic surface active agent comprises palmitamidopropyltrimonium chloride.

7. The method of claim 1, wherein the at least one isolated *Citrus* flavonoid comprises hesperetin and the at least one cationic surface active agent comprises behentrimonium chloride.

8. The method of claim 1, wherein the at least one isolated *Citrus* flavonoid comprises hesperidin and the at least one cationic surface active agent comprises behentrimonium chloride.

9. A method for treating an infestation of head lice in a patient in need thereof by killing the head lice and preventing a final development and a hatching of larvae from lice eggs, the method comprising:
    applying an effective amount of a composition on the hair of the patient, the composition comprising a *Citrus* flavonoid extract and 2 to 7 wt.-% of at least one cationic surface-active agent selected from the group consisting of palmitamidopropyltrimonium chloride and behentrimonium chloride,
    wherein the *Citrus* flavonoid extract provides to the composition about 0.1 to 1 wt.-% of at least one isolated *Citrus* flavonoid selected from the group consisting of naringin, naringenin, hesperetin, and hesperidin.

10. The method of claim 9, wherein the *Citrus* flavonoid extract is obtained by a process consisting of:
    providing a plant material of the genus *Citrus*,
    mixing the plant material with a first solvent to remove essential oils from the plant material,
    separating the first solvent containing the essential oils from the plant material, drying the plant material,
    mixing the plant material with a second solvent,
    concentrating the plant material and the second solvent so as to obtain a syrup,
    adding an acid to the syrup to precipitate at least one *Citrus* flavonoid,
    washing the precipitated at least one *Citrus* flavonoid, and
    drying the washed precipitated at least one *Citrus* flavonoid to obtain the *Citrus* flavonoid extract.

11. The method of claim 9, wherein the composition further comprises 92 to 97.9 wt.-% of additives consisting of:
    at least one surfactant selected from an ionic surfactant, an anionic amphoteric surfactant, a zwitterionic surfactant, and a cationic surfactant, which are each respectively not the at least one cationic surface-active agent,
    at least one of an emulsifier and an emollient,
    at least one vehicle,
    at least one hair conditioning agent,
    at least one preservative, and
    optionally, at least one of an insect killing substance, an antioxidant, a pH adjusting agent, and an adjuvant,
    wherein, the respective wt.-%'s add to 100 wt.-%.

12. The method of claim 9, wherein the at least one cationic surface active agent is palmitamidopropyltrimonium chloride.

13. The method of claim 9, wherein the composition is formulated as a shampoo, a spray, an aerosol, a lotion, a hair conditioner, a gel, a mousse, or as a powder.

14. The method of claim 9, wherein the at least one isolated *Citrus* flavonoid comprises naringin and the at least one cationic surface active agent comprises palmitamidopropyltrimonium chloride.

15. The method of claim 9, wherein the at least one isolated *Citrus* flavonoid comprises naringenin and the at least one cationic surface active agent comprises palmitamidopropyltrimonium chloride.

16. The method of claim 9, wherein the at least one isolated *Citrus* flavonoid comprises hesperetin and the at least one cationic surface active agent comprises behentrimonium chloride.

17. The method of claim 9, wherein the at least one isolated *Citrus* flavonoid comprises hesperidin and the at least one cationic surface active agent comprises behentrimonium chloride.

\* \* \* \* \*